United States Patent [19]

Ogan et al.

[11] Patent Number: 5,569,446
[45] Date of Patent: Oct. 29, 1996

[54] RADIOHALOGENATION OF PROTEINS USING TRIHALOPHENYL DERIVATIVES

[75] Inventors: Marc Ogan, Somerset; Frank P. Tomasella, Englishtown; Jan-I Tu, Lawrenceville, all of N.J.

[73] Assignee: Bracco International B.V., Amsterdam

[21] Appl. No.: 470,332

[22] Filed: Jun. 6, 1995

Related U.S. Application Data

[62] Division of Ser. No. 936,432, Aug. 27, 1992, Pat. No. 5,463,080.

[51] Int. Cl.$^6$ .......................... A61K 47/48; A61K 43/00; A61K 49/04; A61K 49/02; A61K 39/395
[52] U.S. Cl. .................. 424/1.49; 424/1.53; 424/1.69; 424/4; 530/323; 530/324; 530/325; 530/326; 530/327; 530/328; 530/329; 530/330; 530/331; 530/350; 530/388.1; 530/388.25; 530/502; 536/26.6
[58] Field of Search ................................. 424/1.53, 1.69, 424/1.49, 4; 530/323, 324, 325, 326, 327, 328, 329, 330, 331, 350, 388.1, 388.25, 502; 532/26.6

[56] References Cited

U.S. PATENT DOCUMENTS

| | | | |
|---|---|---|---|
| 2,611,786 | 9/1952 | Wallingford | 560/47 X |
| 3,144,479 | 8/1964 | Obendorf | 560/47 |
| 3,359,278 | 12/1967 | Wallingford | 548/545 |
| 3,476,802 | 11/1969 | Holtermann et al. | 560/47 X |
| 3,637,824 | 1/1972 | Holtermann et al. | 560/47 X |
| 3,883,578 | 5/1975 | Gries | 560/47 |
| 4,001,298 | 1/1977 | Gries et al. | 560/47 |
| 4,001,323 | 1/1977 | Felder et al. | 424/5 |
| 4,014,986 | 3/1977 | Tilly et al. | 560/47 X |
| 4,031,088 | 6/1977 | Ackerman | 560/47 X |
| 4,321,368 | 3/1982 | Hoey | 560/74 X |
| 4,735,792 | 4/1988 | Srivastava | 424/1.1 |
| 4,883,650 | 11/1989 | Bhargava et al. | 424/1.1 |
| 4,885,153 | 12/1989 | Wilbur et al. | 424/1.1 |
| 5,047,228 | 9/1991 | Gries et al. | 424/5 |
| 5,089,249 | 2/1992 | Fritzberg et al. | 424/1.1 |

FOREIGN PATENT DOCUMENTS

| | | | |
|---|---|---|---|
| 188692 | 7/1981 | Czechoslovakia | 424/1.1 |
| 0203764 | 12/1986 | European Pat. Off. | 560/47 |
| WO89/11876 | 12/1989 | WIPO | 424/1.1 |
| WO90/03799 | 4/1990 | WIPO | 424/1.1 |

OTHER PUBLICATIONS

Eary et al., Antibodies in Radiodiagnosis and Therapy (Ed. Zalutsky), Chapter 5, Radiochemistry of Halogenated Antibodies, pp. 83–102. (1985).

Keenan et al., Monoclonal Antibiodies in Nuclear Medicine, J. Nucl. Med., 26, pp. 531–537 (1985).

Fritzberg et al., Approaches to Radiolabeling of Antibodies for Diagnosis and Therapy of Cancer, Pharm. Res., vol. 5, No. 6, pp. 325–334 (1988).

Zalutsky et al., Radiohalogenation of a Monoclonal Antibody Using an N–Succinimidyl 3–(Tri–n–butylstannyl)benzoate Intermediate, Cancer Res., 48, pp. 1446–1450 (1988).

Wilbur et al., Development of a Stable Radioiodinating Reagent to Label Monoclonal Antibodies for Radiotherapy of Cancer, J. Nucl. Med., 30, pp. 216–226 (1989).

Srivastava et al., Radioiodinated Iodophenyl Maleimide: A Potential Radioimmunoconjugate with Low In Vivo Deiodination, NucCompact, 20, pp. 145–149 (1989).

Stanko et al., Copper Catalysis on Isotopic Exchange as a Novel Approach to Incorporating Iodine and Bromine into Benzene Derivatives, *Int. J. Radiat. Appl. Instrum. Part A*, 35, pp. 1129–1132 (1984).

Sinn et al., Electrophilic Radioiodine Exchange Labeling in Aqueous Solutions, *Int. J. Radiat. Appl. Instrum. Part A*, 38, pp. 921–925 (1987).

Wilber, D. S., Radiohalogenation of Proteins: An Overview of Radionuclides, Labeling Methods, and Reagents for Conjugate Labeling, *Bioconj. Chem.*, 3, pp. 433–470 (1992).

Bolton et al., The Labelling of Proteins to High Specific Radioactivities by Conjugation to a $^{125}$I–Containing Acylating Agent. Application to Radioimmunoassay, *Biochem. J.*, 133, pp. 529–539 (1973).

*Primary Examiner*—Floyd D. Higel
*Attorney, Agent, or Firm*—George P. Hoare, Jr.; Donald L. Rhoads

[57] ABSTRACT

Compounds, useful as radiolabeling reagents, including a trihalogenated phenyl ring and having the formula

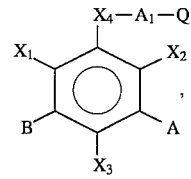

wherein $X_1$, $X_2$ and $X_3$ are halogens, one of which may be a radiohalogen, are disclosed. The invention further includes radiohalogenated proteins as well as processes for preparing such reagents and radiohalogenated proteins.

10 Claims, No Drawings

RADIOHALOGENATION OF PROTEINS USING TRIHALOPHENYL DERIVATIVES

This is a divisional of application Ser. No. 07/936,432, filed Aug. 27, 1992, now U.S. Pat. No. 5,463,080.

FIELD OF THE INVENTION

The present invention relates to the radiolabeling of proteins, and more particularly concerns indirect radiohalogenation processes for proteins including reagents and products pertaining to same.

BACKGROUND OF THE INVENTION

Radiolabeled proteins have been investigated extensively over the past decade for a number of clinical applications. For example, radiolabeled monoclonal antibodies are being developed for therapeutic and diagnostic uses. Monoclonal antibodies having high specificity and affinity for antigens on tumor cell surfaces are considered desirable candidates as carrier molecules to which specific radionuclides can be attached for delivery of radioactivity to a cancer site for therapy or diagnosis.

Radiohalogens are known to possess utility in both therapy and diagnosis. For example $^{123}$I has been proven useful for imaging, while $^{131}$I can be used for imaging and more preferably for radiotherapy. Bromine radionuclides $^{75}$Br and $^{76}$Br are also useful in diagnosis, while $^{77}$Br is used in radiotherapy. Fluorine-18 ($^{18}$F) and astatine-211 (211At) are also utilized in diagnostics and radiotherapy.

Processes for directly labeling proteins, such as antibodies, have proven to be difficult. Typically, the strong oxidation conditions involved in direct radiolabeling of an antibody have substantial adverse effects on the biological activity of the antibody. It is also known that radiohalogenation of antibodies occurs primiarily at the tyrosyl residues providing a less than stable bond. In vivo dehalogenation, rendering the imaging or therapeutic agent useless and causing possible toxicity to the patient may result.

Improvements have been realized with the development of indirect labeling techniques. These involve the prelabeling of a small molecule suitable for subsequent conjugation to a protein. An early series of small molecules useful for indirect labeling includes a phenol group for facile introduction of the radiohalogen. The exemplary member of this group is the commercially available Bolton-Hunter reagent While these reagents greatly reduce the protein-damaging chemistry used in the direct labeling techniques, in vivo deiodination is still a problem. More recent reagents for indirect labeling include succinimidyl para-iodobenzoate and succinimidyl para-iodophenylpropionate U.S. Pat. No. 4,885,153 discloses indirect radiohalogenating reagents of the formula

*X—Ar—R where *X is a radiohalogen, Ar is an aromatic or heteroaromatic ring which may include polar substituents, e.g., nitro, sulfonic acid, carboxylic acid or dialkylamino, and R is a short chain substituent which includes a functional group for conjugation to a protein.

SUMMARY OF THE INVENTION

In accordance with the present invention it has now been found that compounds including a trihalo-phenyl group, where at least one of the halogens is a radionuclide, are useful for indirect radiohalogenation of proteins, e.g., monoclonal antibodies. The present compounds have the general structure where $X_1$, $X_2$ and $X_3$ are independently selected from the halogens, and where one of $X_1$, $X_2$ and $X_3$ may be a radiohalogen;

$X_4$ is a linking group;

$A_1$ is a single bond or a $C_{1-12}$alkyl spacer group;

Q is a functional group suitable for conjugation to a protein which may include a leaving group;

A and B are independently hydrogen or a group selected from $$-CH_2-\overset{R_1}{\underset{|}{N}}-R_2, \quad -\overset{O}{\underset{\|}{C}}-\overset{R_1}{\underset{|}{N}}-R_2 \text{ or } -\overset{O}{\underset{\|}{C}}R_3;$$

$R_1$ and $R_2$ are independently selected from hydrogen, alkyl, hydroxyalkyl and acyloxyalkyl;

$R_3$ is —OH, —O-alkyl, —O-hydroxyalkyl, —O-alkoxyalkyl, —O-aminoalkyl, —NH-hydroxyalkyl and —NH-carboxyalkyl.

The

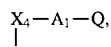

i.e., linkage-spacer-functional group, chain is well-known and is described for example in U.S. Pat. No. 4,885,153 incorporated herein by reference.

Processes for preparing the above compounds, processes using such compounds and the radiohalogenated proteins resulting therefrom are also a part of this invention.

DETAILED DESCRIPTION OF THE INVENTION

The present compounds useful as radiolabeling reagents, provide excellent in vivo stability against dehalogenation. Also, the process which uses these radiolabels to prepare radiolabeled proteins is a mild technique which is therefore protective of the biological activity of the protein. While the exact mechanism is not known, the enhanced protection against dehalogenation provided herein is believed to be attributable to the increased electronic stability of proteins radiolabeled using compounds of formula I.

The novel radiohalogenated proteins of the present invention have the general formula

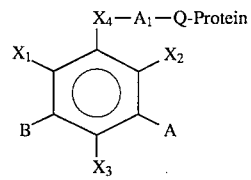
II wherein at least one of $X_1$, $X_2$ and $X_3$ is a radiohalogen and the others are independently halogen, preferably I or Br, and where A, B, $A_1$ and Q are as defined above for formula I. As mentioned above, the protein may be linked to the functional group, Q, via a carrier.

Linking groups for $X_4$ can be any group known to provide linkage to an aryl moiety including amines, carbonyls, amides, reverse amides, carbamates, ureas and ethers. These exemplary linking groups may also be expressed, respectively,

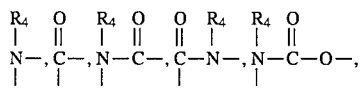

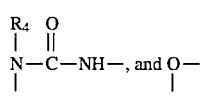

where $R_4$ is H or alkyl. Such linking groups are well known and are disclosed, e.g., in U.S. Pat. No. 4,885,153.

Functional groups for Q are also known and disclosed, e.g., in U.S. Pat. No. 4,885,153. Suitable functional groups which have leaving groups include

| | |
|---|---|
| esters (including phenolic esters and acylsuccinimides) | 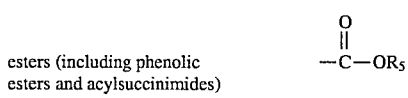 |
| imide esters |  |
| imidate esters | $\begin{array}{c}NH\\\|\\-C-O\text{-alkyl}\end{array}$ |
| anhydrides | $\begin{array}{c}O\quad O\\\|\quad\|\\-C-O-C\text{-alkyl}\end{array}$ |
| alkylhalides | $-(CH_2)_{1-5}-CH_2\text{-halogen}$ | where the leaving group is $-OR_5$, halogen $-O$-alkyl or $$-OCalkyl$$ (with C=O)

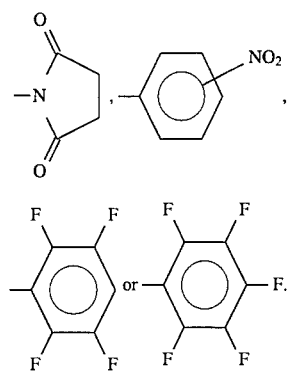

Suitable functional groups, Q, which do not have leaving groups include

| | |
|---|---|
| aldehydes | $-\overset{O}{\underset{\|}{C}}H$ |
| isothiocyanates | $-N{=}C{=}S$ |
| thiols | $-SH$ |
| diazos | $-N_2^+$ |
| amines | $NH_2$ |
| hydrazines | $-NHNH_2$ |
| maleimides | 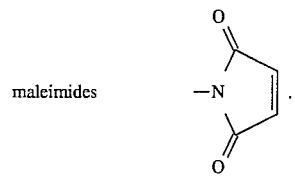 |

The term radiohalogen as used herein for compounds of formula I, formula II and throughout this application refers to any radionuclide of any of the halogens. Exemplary radiohalogens include radionuclides of iodine, bromine, fluorine and astatine; and, more specifically, may include $^{123}I$, $^{125}I$, $^{131}I$, $^{75}Br$, $^{77}Br$, $^{18}F$ and $^{211}At$.

The term protein as used herein refers to any protein requiring conjugation with a radionuclide including but not limited to monoclonal antibodies and plasma proteins, polypeptides, hormones, carbohydrates and the like. Exemplary monoclonal antibodies include ChiL6, ChiBR96, murine L6, murine BR96 as disclosed in the following references: Lui A. Y., Robinson R. R., Hellstrom K. E., Murray D. Jr., Chang C. P., and Hellstrom I. Chimeric Mouse-Human IgG$_1$ Antibody that can Mediate Lysis of Cancer Cells Proc. Natl. Acad. Sci. USA 1987, 84, 3439–3443; Hellstrom I., Garrigues H. J., Garrigues U., and Hellstrom K. E. Internalizing Mouse Monoclonal Antibodies to Le$^y$-Related Cell Surface Antigens Cancer Res 1990, 50, 2183–2190; and Hellstrom I., Beaumier P. L., and Hellstrom K. E. Antitumor Effects of L6, an IgG$_{2a}$ Antibody Reacting with Most Human Carcinomas Proc Natl Acad Sci USA 1986, 83, 7059–7063.

The term carrier as used herein refers to any group coupled to a protein which can also be coupled to another molecule to provide a linkage between the protein and molecule. Suitable carriers include amino acid polymers, e.g., polylysine, carbohydrates, and the like.

The term alkyl as used herein, by itself or as part of another group, refers to branched and straight chain groups of up to 12 carbon atoms, and preferably of 1 to 8 carbons.

The term hydroxyalkyl as used herein refers to (monohydroxy)alkyl or (polyhydroxy)alkyl. Exemplary groups include

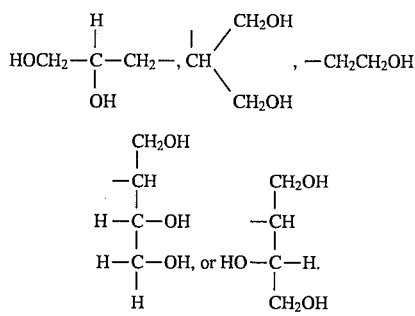

Compounds of formula I are readily prepared using known methodology. For example, to prepare compounds of formula I where $X_4$ is

and Q is

first a compound of the formula

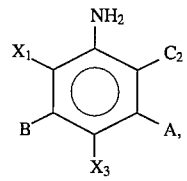                                             III where $X_1$, $X_2$ and $X_3$ are each halogen, is reacted with a compound of the formula

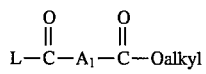                                             IV in a solvent, e.g., dimethylacetamide, (where L is a leaving group, e.g., halogen), such as methyl-4-(chloroformyl)butyrate

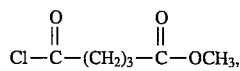                                             IV' to provide

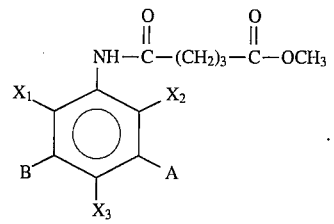                                             V

Intermediates where $R_4$ is other than hydrogen

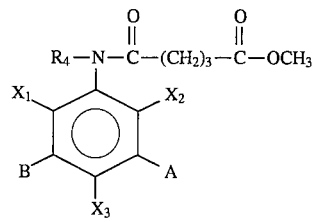                                             Va can be prepared from compound V by known methodology, e.g., standard alkylation techniques and the like. For example, compound V can be treated with NaOCH$_3$ in solvents, e.g., dimethylformamide and methanol followed by treatment with methiiodide to provide intermediates of Va where $R_4$ is methyl.

The intermediates of formula V or Va are readily converted to the products of formula I where Q is

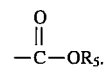

For example, the compound of formula V can be subjected to standard hydrolytic procedures, e.g., treatment with a base in one or more solvents, to provide

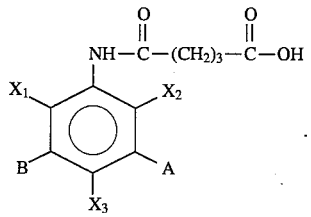                                             Ia

Further, the acid of formula Ia can be treated with O-(N-succinimidyl)-N,N,N',N'-tetramethyluronium tetrafluoroborate in a solvent and in the presence of an organic base to provide

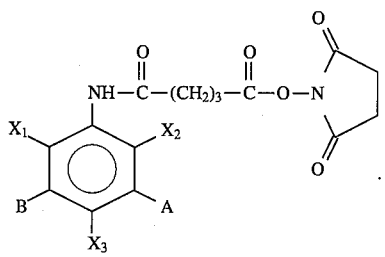                                             Ib

Well established procedures are also used to prepare other embodiments of formula I, For example the compounds of formula I where $X_4$ is

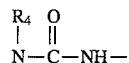

and Q is

can be prepared by first reacting a compound of formula III with phosgene in a solvent, e.g., toluene, to provide

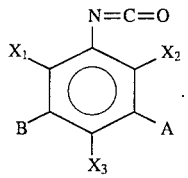 VI

Intermediate VI is thereafter reacted with a compound of the formula

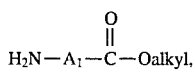 VII such as glycine ethyl ester

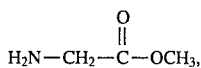 VII' in a solvent, such as tetrahydrofuran, to provide

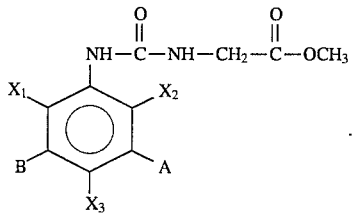 VIII

The formula VIII esters are converted to the desired products of formula I where Q is

using the techniques described above.

The compounds of formula III are known or can be prepared from known compounds using known techniques. For example, triiodinated phenyl compounds are well known in the x-ray contrast art. Techniques for preparing triiondinated phenyl comunds are readily available in EP 431,838 to Banganajan et al. wherein compounds are disclosed having the formula

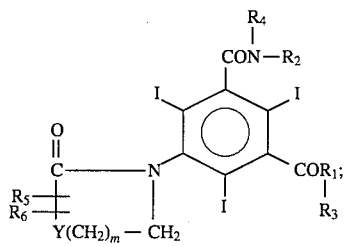

U.S. Pat. No. 4,001,323 to Felder et al. wherein compounds are disclosed having the formula

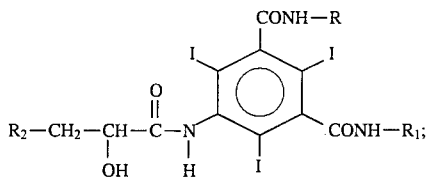

U.S. Pat. No. 3,701,771 disclosing compounds of the formula

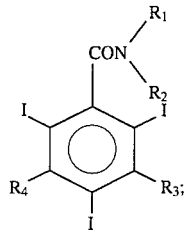

U.S. Pat. No. 3,883,535 disclosing compounds of the formula

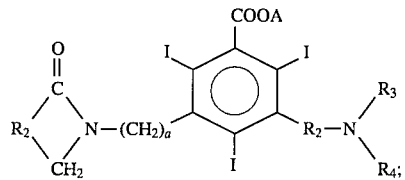

U.S. Pat. No. 4,352,788 disclosing compounds of the formula

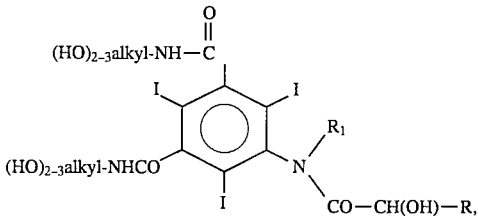

and the like.

The desired trihalophenyl compound is typically radiolabeled prior to conjugation with the desired protein using procedures such as those described by Sinn H., Schrenk H. H., Clorius J. H., and Maier-Borst W. Electrophilic Radioiodine Exchange Labeling in Aqueous Solutions. Int. J. Radiat. Appl. Instrum. Part A 1987, 38, 921–925; Hradilek P., Kronrad L., Kopicka K., Radioactive Iodine Derivatives of Hippuric Acid. Patent CS 188692. CA96(15):1233020; Sinn H., Maier-Borst W., Elias H. A Fast and Efficient Method for Labelling Radiographic Contrast Media with $^{121}I$ and $^{123}I$. Int. J. Appl. Radiat. & Isotopes 1979, 30, 511–512; and Thakur M. L., The Preparation of Iodine-123 Labelled Contrast Agents. Int. J. Appl. Radiat. Isotopes 1974, 25, 576–578. For example, a desired compound of formula I can be treated with a source of radionuclide such as $Na^{125}I$ in one or more solvents and in the presence of a catalyst, e.g., HCl, $H_3PO_4$, $HAuCl_4$, $H_2PtCl_6$. Such procedures may typically incude the use of a phosphate buffer solution and are carried out in protic solvents such as water, methanol, ethanol or mixtures thereof, or non-protic solvents, e.g., $CCl_4$. Acetic acid/solvent mixtures are also known to be employed when treating with the source of radionuclide to prevent unwanted hydrolysis of compound I.

Compounds of formula I where $R_5$ is hydrogen can be labeled and thereafter converted to products where $R_5$ is other than hydrogen. Alternatively, the products of formula I where $R_5$ is other than hydrogen can be labeled as a last step prior to conjugation.

Conjugation of the radiolabels of formula I of this invention with the desired protein is conveniently carried out by reacting an appropriate source of protein in the presence of a solvent with the radiolabeled compound of formula I, typically in the presence of an aqueous buffer solution to maintain a mild pH, preferably pH ~9.

Preferred radiolabeling reagents of the present invention are those of formula I wherein
two of $X_1$, $X_2$ and $X_3$ are each iodine and the other is a radionuclide of iodine;
$X_4$ is $$-\underset{\underset{R_4}{|}}{N}-\underset{\underset{}{||}}{C}-\quad \text{or} \quad -\underset{\underset{R_4}{|}}{N}-\underset{\underset{}{||}}{C}-NH-$$

$A_1$ is $C_{1-12}$alkyl;
Q is $$-\underset{\underset{}{||}}{C}-OR_5;$$

and,
A and B are independently $$-\underset{\underset{}{||}}{C}-\underset{\underset{R_2}{|}}{N}-R_2 \quad \text{or} \quad -\underset{\underset{}{||}}{C}-R_3$$

Most preferred are the preferred compounds of formula I above where
A is $C_{1-3}$alkyl;
Q is $$-\underset{\underset{}{||}}{C}-OH \quad \text{or} \quad -\underset{\underset{}{||}}{C}-O-N\underset{\underset{O}{\diagdown}}{\diagup}\!\!\!\!\!\!\!\!\!\!\!\!\!\!\!\!\!\!\!\!\!\!\!\!\!\!\!\!\!\!\!\!;$$

$R_1$ is hydrogen or alkyl;
$R_2$ is hydroxyalkyl or alkyl; and
$R_3$ is —O-alkyl or —O-hydroxyalkyl.

The preferred radiolabeled proteins in accordance with the present invention are those "preferred" and "most preferred" reagents above, conjugated with the chimeric monoclonal antibody L6 and the chimeric monoclonal antibody BR96.

EXAMPLE 1

5-[(4-Carboxy-1-oxobutyl)amino]-2,4,6-triiodo-1,3-benzenedicarboxylic acid, dimethyl ester A. 5-[(5-Methoxy-1,5-dioxopentyl)amino]-2,4,6-triiodo-1,3-benzenedicarboxylic acid, dimethyl ester To a stirred solution of 5-amino-2,4,6-triiodo-1,3-benzenedicarboxylic acid, dimethyl ester (505.5 mg, 1.52 mmol) in 5 mL of dimethylacetamide ws added methyl (4-chloroformyl)butyrate (307.4 mg, 1.87 mmol). After 4 hours, an additional 101.3 mg (0.62 mmol) of (4-chloroformyl)butyrate was added and the solution was stirred protected from from light at room temperature for 3 days. The solution was poured into a separatory funnel containing 20 mL of half saturated sodium hydrogen carbonate and extracted with 2×20 mL of ethyl acetate. The combined organic phase was extracted with 2×20 mL of water, 1×20 mL of brine, dried over anhydrous magnesium sulfate, filtered and evaporated in vacuo to afford the crude triester as a residue. The crude product was crystallized from ethyl acetate/hexane to yield 553.0 mg of the triester.

Analysis calc'd for $C_{16}H_{16}I_3NO_7 \cdot 0.4EtOAc$: C, 28.18; H, 2.56; N, 1.87; I, 50.74; Found: C, 28.42; H, 2.26; N, 1.83; I, 50.67.

B. 5-[(4-Carboxy-1-oxobutyl)amino]-2,4,6-triiodo- 1,3-benzenedicarboxylic acid, dimethyl ester To a solution of methyl triester of part A (60.9 mg, 0.09 mmol) in 3 mL MeOH was added 2 mL of 0.5M NaOH. The solution was stirred at room temperature under $N_2$ and protected from light for 3 hours. The reaction was poured into a separatory funnel with 5 mL of $H_2O$ and extracted with 1×5 mL EtOAc. The aqueous phase was acidified to pH 2 with 5 mL of 1M HCl and further extracted with 3×5 mL of EtOAc. The combined organic phase was dried ($MgSO_4$), filtered and evaported in vacuo to afford 52.9 mg of crude product. The crude product was crystallized from EtOAc/hexane (1:1) to yield 49.1 mg of the methyl acid.

Analysis calc'd for $C_{15}H_{14}I_3NO_7$: C, 25.70; H, 2.01; N, 2.00; Found: C, 25.57; H, 1.92; N, 2.28.

EXAMPLE 2

[I-125]-5-[(4-Carboxy-1-oxobutyl)amino]-2,4,6-triiodo-1,3-benzenedicarboxylic acid, dimethyl ester A 1 mL vial was charged with the title compound of Example 1 (60 ug, 0.09 umol) dissolved in 40 mL 50 mM phosphate pH 9.1. To this was added 5 uL (250 uCi) of $Na^{125}I$ followed by 5 uL (5 ug, 0.02 umol) of a 2.9 mM solution of $HAuCl_4$ in 1M HCl. The reaction was heated for 1 hour at 100° C. HPLC analysis showed the radiochemical yield of 64%. HPLC (Zorbax Sil, 4.6×150 mm; EtOAc/hexane/HOAc (50:50:1); 1.0 mL/min; UV 254 nm and radiometric detection) tr 8.9 min.

EXAMPLE 3

Labeled Murine L6 with
[I-125]-5-[(4-Carboxy-1-oxybutyl)amino]-2,4,6-triiodo-1,3-benzenedicarboxylic acid, dimethyl ester A. ([I-125]-5-[(4-Carboxy-1-oxobutyl)amino]- 2,4,6-triiodo-1,3-benzenedicarboxylic acid, dimethyl ester)

To a solution of the radioiodinated product of Example 2 (8 ug, 0.01 umol, 35 uCi) in 40 uL of ethyl acetate was added 20 uL (60 ug, 0.2 umol) of a 10 mM solution of diisopropylethylamine in $CH_3CN$ followed by 20 uL (26 ug, 0.2 umol) of a 10 mM solution of O-(N-succinimidyl)-N,N,N',N'-tetramethyluronium tetrafluoroborate in $CH_3CN$. The solution was stirred at room temperature for 30 minutes, then analyzed by HPLC (Zorbax Sil, 4.6×150 mm; EtOAc/hexane/HOAc (60:40:1); 1.0 mL/min, radiometric detection; tr 8.1 min). Radiochemical yield of the activated title A ester was 33%.

B. Labeled Murine L6 with [I-125]-5-[(4-Carboxy-1-oxobutyl)amino]-2,4,6-triiodo-1,3-benzenedicarboxylic acid, dimethyl ester The organic solvent containing the title A compound was evaporated to dryness under a stream of nitrogen gas. A solution of murine L6 antibody (280 ug, $1.9 \times 10^{-3}$ umol) in 20 uL of 50 mM phosphate buffer pH 7.4 was diluted wit 40 uL of 250 mM borate buffer pH 8.5, and the resulting antibody solution (pH 8.5) was added to the radiolabeled activated ester of part A. The reaction was stirred for 90 minutes, then analyzed by size exclusion HPLC (Phenomenex TSK3000 7.5×300 mm; 10 mM phosphate pH 7.4, 150 mM NaCl, 1.0 mL/min; UV 280 nm and radiometric detection; tr 7.4 min). The L6 conjugate was purified by HPLC (Phenomenex TSK3000 7.5×300 mm; 10 mM phosphate pH 7.4, 150 mM NaCl, 1.0 mL/min; UV 280 nm and radiometric detection; tr 7.4 min).

EXAMPLE 4

Labeled ChiL6 with
[I-125]-5-[(4-Carboxy-1-oxobutyl)-amino]-2,4,6-triiodo-1,3-benzenedicarboxylic acid, dimethy ester A. ([I-125]-5-[(4-Carboxy-1-oxobutyl)-amino]- 2,4,6-triiodo-1,3-benzenedicarboxylic acid, dimethyl ester)

A solution of the product of Example 2 (20 ug, 0.03 umol, 200 uCi) in 100 uL of ethyl acetate was evaporated to dryness under a stream of nitrogen gas. The residue was three times dissolved in 100 uL of $CH_3CN$ and evaporated to dryness with nitrogen gas. To the residue added 20 uL (60 ug, 0.2 umol) of a 10 mM solution of diisopropylethylamine in $CH_3CN$ followed by 20 uL (26 ug, 0.2 umol) of a 10 mM solution of O-(N-succinimidyl)-N,N,N',N'-tetramethyluronium tetrafluoroborate in $CH_3CN$. The solution was stirred at room temperature for 10 minutes, then analyzexd by HPLC (Zorbax Sil, 4.6×150 mm; EtOAc/hexane/HOAc (60:40:1); 1.0 mL/min, radiometric detection; tr 8.1 min). Radiochemical yield of the activated title A ester was 21%.

B. Labeled ChiL6 with [I-125]-5-[(4-Carboxy-1-oxobutyl)amino]-2,4,6-triiodo-1,3-benzenedicarboxylic acid, dimethyl ester The organic solvent containing part A compound was evaporated to dryness under a stream of nitrogen gas. A solution of ChiL6 antibody (100 ug) in 20 uL of 50 mM phosphate buffer pH 7.4 was diluted with 40 uL of 250 mM borate buffer pH 8.5, and the resulting antibody solution (pH 8.5) was added to the radiolabeled activated ester of part A. The reaction was stirred for 2 hours, then analyzed by size exclusion HPLC (Phenomenex TSK3000) 7.5×300 mm; 10 mM phosphate pH 7.4, 150 mM NaCl, 1.0 mL/min; UV 280 mm and radiometric detection; tr 6.3 min). The ChiL6 conjugate was purified by Sephadex G-25 chromatography eluting with PBS to afford 4.0 uCi of labeled antibody.

EXAMPLE 5

5-[(4-Carboxy-1-oxobutyl)methylamino]-2,4,6-triiodo-1,3-benzenedicarboxylic acid, dimethyl ester A. 5-[(5-Methoxy-1,5-dioxopentyl)methylamino]- 2,4,6-triiodo-1,3-benzenedicarboxylic acid, dimethyl ester To an ice cooled solution of the trimethyl ester of Example 1, part A (103.9 mg, 0.15 mmol) in 1.0 mL of dimethylformamide was added a solution of NaOMe (13.0 mg, 0.24 mmol) in 0.3 mL of dry methanol. The solution was stirred at 0° C. under nitrogen gas for 15 minutes, then a solution of MeI (65.7 mg, 0.46 mmol) in 1.5 mL of dimethylformamide was added. The solution was warmed to room temperature and further stirred for 2 hours. The reaction was poured into a separatory funnel with 10 mL of ethyl acetate and extracted with 2×10 mL of water and 1×10 mL of brine. The combined organic phase was filtered through a cone of anhydrous magnesium sulfate and evaporated in vacuo to afford 97.6 mg of crude product as a white solid. The solid was washed with 2 mL of ethyl ether to yield 85.9 mg of N-methyl triester.

Analysis calc'd for $C_{17}H_{18}I_3NO_7$: C, 28.01; H, 2.49; N, 1.92; I, 52.22; Found: C, 28.22; H, 2.10; N, 1.85; I, 51.38.

B. 5-[(4-Carboxy-1-oxobutyl)methylamino]-2,4,6-triiodo-1,3-benzenedicarboxylic acid, dimethyl ester To a solution of the title A N-methyl triester (29.5 mg, 0.04 mmol) in 2 mL methanol was added 1 mL of 0.25M sodium hydroxide. The solution was stirred at room temperature under nitrogen gas and protected from light for 3 hours. The reaction was poured into a separatory funnel with 5 mL of water and extracted with 1×5 mL ethyl acetate. The aqueous phase was acidified to pH 2 with 2 mL of 1M hydrochloric acid and further extracted with 3×5 mL of ethyl acetate. The combined organic phase was dried over anhydrous magnesium sulfate, filtered and evaported in vacuo to afford 29.1 mg of crude product. The crude product was crystallized from ethyl acetate/hexane (1:1) to yield 25.7 mg of the N-methyl acid.

Analysis calc'd for $C_{16}H_{16}I_3NO_7$: C, 26.88; H, 2.26; N, 1.96; I, 53.25; Found: C, 27.26; H, 2.16; N, 1.96; I, 52.98.

EXAMPLE 6

[I-125]-5-[(4-Carboxy-1-oxobutyl)methylamino]-2,4,6-triiodo- 1,3-benzenedicarboxylic acid, dimethyl ester A 1 mL Reacti-Vial was charged with a solution of N-methyl acid of Example 5 (7.9 ug, 0.01 umol) in 5 uL of EtOAc. The EtOAc was evaporated under a stream of nitrogen gas. To the residue was added 30 uL of 50 mM phosphate buffer pH 9.0 and the vial was then sonicated for 5 minutes. To this solution was added 5 uL (2.5 mCi) of $Na^{125}I$ followed by 5 uL (5 ug, 0.02 umol) of a 2.9 mM solution of $HAuCl_4$ in 1M hydrochloric acid. The reaction was heated for 7 hours at 100° C. The reaction was cooled to room temperature and then a solution of $AgNO_3$ (2.0 mg, 0.01 mmol) in 40 uL water was added to precipitate AgCl. The aqueous mixture was acidified by addition of 20 uL of 0.5M $HNO_3$ and extracted with 2×150 uL of ethyl acetate. The combined ethyl acetate layer was filtered through a 0.4 filter packed with anhydrous magnesium sulfate. This ethyl acetate fraction contained approximately 800 uCi of radioactivity. HPLC showed radiochemical purity to be 75%. The overall radiochemical yield was 24%. The nominal specific activity was 54 mCi/umol. HPLC (Zorbax Sil, 4.6×150 mm; EtOAc/hexane/TFA (35:65:0.1); 1.0 mL/min; UV 254 nm and radiometric detection) tr 26 min.

EXAMPLE 7

[I-125]-5-[[5-[(1,5-Dioxo-1-pyrrolidinyl)oxy]-1,5-dioxopentyl]methylamino]-2,4,6-triiodo-1,3-benzenedicarboxylic acid, dimethyl ester To a solution of crude product of Example 6 (0.5 ug, $7.0 \times 10^{-4}$ umol) (12.5 uCi, radiochemical purity 34%) in 10 uL of ethyl acetate was added 20 uL (60 ug, 0.2 umol) of a 10 mM solution of diisopropyl-ethylamine in CH₃CN followed by 20 uL (26 ug, 0.2 umol) of a 10 mM solution of O-(N-succinimidyl)-N,N,N',N'-tetramethyluronium tetrafluoroborate in CH3CN. The solution was stirred at room temperature for 15 minutes, then analyzed by HPLC (Zorbax Sil, 4.6×150 mm; EtOAc/hexane/HOAc (60:40:0.6); 1.0 mL/min, radiometric detection; tr 12.3 min). Overall radiochemical yield of the activated ester was 33% indicating quantitative conversion of the acid to the active ester.

EXAMPLE 8

Labeled ChiBR96 with
[I-125]-5-[(4-Carboxy-1-oxobutyl) methylamino]-2,4,6-triiodo-1,3-benzenedicarboxylic acid, dimethyl ester A solution of the Example 6 product (800 uCi, 7.9 ug, 0.01 umol) in 150 uL of ethyl acetate was evaporated under a stream of nitrogen gas. The residue was twice dissolved in 150 uL of CH₃CN and evaporated to dryness under a stream of nitrogen gas. To the residue was added a solution of N-hydroxy-succinimide (12 ug, 0.10 umol) in 12 uL of CH₃CN followed by a solution of 1-(3-dimethylaminopropyl)- 3-ethylcarbodiimide hydrochloride (20 ug, 0.10 umol) in 20 uL of CH₃CN. The reaction was stirred at room temperature for 3 hours, then the solvent was evaporated under a stream of nitrogen gas. To the residue was added a solution of ChiBR96 (200 ug, 1.3× $10^{-3}$ umol) in 100 uL of 140 mM phosphate buffer pH 9.0. The reaction was stirred for 1 hour, then 100 uL of 250 mM Tris acetate buffer pH 7.0 was added. Size exclusion HPLC (Phenomenex TSK3000 7.5×300 mm; 10 mM phosphate pH 7.4, 150 mM NaCl, 1.0 mL/min; UV 280 nm and radiometric detection; tr 7.5 min) showed the conjugation efficiency to be 2.5%. The ChiBR96 conjugate was purified by FPLC (Pharmacia Superose 6HR 10/30 10×300 mm; 10 mM phosphate pH 7.4, 150 mM NaCl, 0.5 mL/min; UV 280 nm and radiometric detection; tr 31 min). The isolated ChiBR96 conjugate had 99% radiochemical purity as determined by TSK3000 size exclusion HPLC.

EXAMPLE 9

Labeled ChiL6 with
[I-125]-5-[(4-Carboxy-1-oxobutyl)methylamino]-2,4,6-triiodo-1,3-benzenedicarboxylic acid, dimethyl ester A solution of the Example 6 product (80 uCi, 8.0 ug, 0.01 umol) in 80 uL of ethyl acetate was reduced in volume to 20 uL under a stream of nitrogen gas. To the residue was added a solution of N-hydroxysuccinimide (10 ug, 0.09 umol) in 10 uL of CH₃CN followed by a solution of 1-(3-dimethylamino-propyl)- 3-ethylcarbodiimide hydrochloride (15 ug, 0.08 umol) in 15 uL of CH₃CN. The reaction was stirred at room temperature for 3 hours, then the solvent was evaporated under a stream of nitrogen gas. To the residue was added a solution of ChiL6 (100 ug, 16.7×$10^{-4}$ umol) in 40 uL of 125 mM phosphate buffer pH 9.0. The reaction was stirred for 1 hour, then 100 uL of 250 mM Tris acetate buffer pH 7.0 was added. Size exclusion HPLC (Phenomenex TSK3000 7.5×300 mm; 10 mM phosphate pH 7.4, 150 mM NaCl, 1.0 mL/min; UV 280 nm and radiometric detection; tr 7.5 min) showed the conjugation efficiency to be 12%. The ChiL6 conjugate was purified by FPLC (Pharmacia Superose 6HR 10/30 10×300 mm; 10 mM phosphate pH 7.4, 150 mM NaCl, 0.5 mL/min; UV 280 nm and radiometric etection; tr 34 min). The isolated ChiL6 conjugate had 99% radiochemical purify as determined by TSK3000 size exclusion HPLC.

EXAMPLE 10

5-[(4-Carboxy-1-oxobutyl)-amino]-2,4,6-triiodo-1,3-benzenedicarboxylic acid

A. 5-[(5-Methoxy-1,5-dioxopentyl)amino]-2,4,6-triiodo-1,3-benzenedicarboxylic acid, Diacid chloride To an ice cool stirred solution of 5-amino- 2,4,6-triiodo-1,3-benzenedicarboxylic acid, diacid chloride (2.7 g, 4.6 mmol) in 3 mL of dimethylacetamide was added methyl (4-chloroformyl)butyrate (1.5 g, 9.0 mmol). The solution was stirred for 18 hours at room temperature. The reaction mixture ws poured into 25 mL of water and extracted with 3×15 mL of ethyl acetate. The combined organic phase was extracted with 2×10 mL of water, dried over anhydrous magnesium sulfate, filtered and evaporated in vacuo to afford the desired product as a residue. The crude product was crystallized from CH₃CN to yield 1.35 g of the title A compound, i.e., the isophthalyl chloride. The product was used without further purification.

B. 5-[(4-Carboxy-1-oxobutyl)-amino]-2,4,6-triiodo- 1,3-benzenedicarboxylic acid

A solution of isophthalyl chloride of part A (0.5 g, 0.07 mmol) in 20 mL of 0.2M sodium hydroxide was stirred at room temperature for 18 hours. The solution was then adjusted to pH 2.0 with 2M HCl and extracted with 3×30 mL of ethyl acetate, dried over anhydrous magnesium sulfate, filtered and evaporated in vacuo to afford 0.13 g of the desired tricarboxylic acid as a solid.

Analysis calc'd for $C_{13}H_{10}I_3NO_7 \cdot 0.10EtOAc$: C, 23.61; H, 1.60; N, 2.05; I, 55.84; Found: C, 23.98; H, 1.68; N, 2.04; I, 55.44.

EXAMPLE 11

[I-125]-5-[(4-Carboxy-1-oxobutyl)amino]-2,4,6-triiodo-1,3-benzenedicarboxylic acid A solution of the triacid product of Example 10 (100 ug, 0.15 umol) and Na$^{125}$I (100 uCi) in 30 uL of water was heated to 80° C. for 2.5 hours. Radiochemical yield of the resultant I-125-triacid, determined by analytic HPLC, was 100%. HPLC (Zorbax Amine, 4.6×150 mm, 50 mM phosphate pH 6.0/CH₃CN (70:30); 1.0 mL/min; UV 254 and radiometric) tr 16.9 min.

EXAMPLE 12

5-[[[(2-Carboxymethy)amino]carbonyl]amino]-2,4,6-triiodo- 1,3-benzenedicarboxylic acid, dimethyl ester A. 5-[[[(2-Methoxy-2-oxoethyl)amino]carbonyl]-amino]-2,4,6-triiodo-1,3-benzenedicarboxylic acid, dimethyl ester To a solution of 5-amino-2,4,6-triiodo-1,3-benzenedicarboxylic acid, dimethyl ester (189.3 mg, 0.37 mmol) in 3 mL of tetrahydrofuran was added 1.9M solution of phosgene (0.5 mL, 0.95 mmol) in toluene. The reaction was capped with a septum and stirred at 50° C. overnight. The solution was evaporated to a residue under a stream of nitrogen gas. The residue was dissolved in 1 mL of tetrahydrofuran and glycine ethyl ester (72.7 mg, 0.71 mmol) was added as a solid. The resulting solution was stirred under nitrogen gas for 4 hours to afford a thick precipitate. The solid was isolated and washed with 2×5 mL of ethyl ether, and dried under vacuum to afford 202.8 mg of crude product. A sample of 20.5 mg of crude product was crystallized from ethyl acetate/hexane to yield 14.2 mg of the glycidylurea product.

Analysis calc'd for $C_{15}H_{15}I_3N_2O_7 \cdot 0.1EtOAc$: C, 25.52; H, 2.20; N, 3.86; I, 52.25; Found: C, 25.89; H, 2.03; N, 3.77; I, 53.13.

B. 5-[[[(2-Carboxymethy)amino]carbonyl]amino]- 2,4,6-triiodo-1,2-benzenedicarboxylic acid, dimethyl ester To a solution of the glycidyl ester of part A (34.0 mg, 0.05 mmol) in 2 mL of methanol was added 0.2 mL of 0.2M sodium hydroxide. The reaction was stirred at room temperature for 3 hours. The solution was then poured into a separatory funnel with 5 mL of 2M hydrochloric acid and extracted with 2×10 mL of ethyl acetate. The combined organic phase was extracted with 2×10 mL water, 1×10 mL brine, dried over anhydrous magnesium sulfate, filtered and evaporated in vacuo to afford the desired glycidyl acid as a solid. Rf 0.20. MS (FAB$^+$): 688 (M+H). $^1$H NMR ($D_6$-DMSO): 8.45 (s, 1H, NH), 6.64 (br s, 1H, NH), 3.89 (s, 6H, ArCO$_2$CH$_3$), 3.79 (mult, 2H, CH$_2$CO$_2$H).

EXAMPLE 13

N,N'-bis(isopropyl)-5-[(4-Carboxy-1-oxobutyl)amino]-2,4,6-triiodo-1,3-benzenedicarboxyamide A. N,N'-bis(isopropyl)-5-Amino-2,4,6-triiodo-1,3-benzenedicarboxamide To an ice cool stirred solution of 5-amino- 2,4,6-triiodo-1,3-benzenedicarboxylic acid, diacid chloride (1.17 g, 2.0 mmol) in 1 mL of dimethylacetamide was added isopropylamine (1.18 g, 20.0 mmol). The solution was stirred at room temperature for 18 hours. The reaction mixture was poured into 20 mL of acetone which resulted in the precipitation of a white solid. The precipitate was filtered, washed with 5 mL acetone and dried in vacuo. The crude title A product was 0.75 g which was used without further purification. TLC (EtOAc/hexane (2:3)) rf 0.6. MS (FAB$^+$): 642 (M+H).

B. N,N'-bis(isopropyl)-5-[(4-carbomethoxy-1-oxobutyl)amino]-2,4,6-triiodo-1,3-benzenedicarboxyamide To an ice cool stirred solution of diisopropyl-5-aminobenzenedicarboxamide (0.63 g, 0.98 mmol) in 1.2 mL of dimethylacetamide was added methyl (4-chloroformyl)butyrate (0.33 g, 2.0 mmol). The solution was stirred at room temperature for 18 hours. The reaction mixture was poured into 20 mL of CH$_3$CN and warmed slightly to dissolve all the solid material. Upon standing, a crude material crystallized. The precipitate was filtered, washed with 2×10 mL CH$_3$CN and dried in vacuo. The yield of the crude product was 0.40 g. No further purification was attempted. TLC (EtOAc/hexane (2:3)) rf 0.1. MS (FAB$^+$): 770 (M+H). $^1$H MR (D$_6$-DMSO): 9.92 (s, 1H, NH), 8.46 (d, 1H, iprNHCO), 8.36 (d, 1H, iprNHCO), 4.01 (m, 2H, CH(CH$_3$)$_2$), 3.60 (s, 3H, CO$_2$CH$_3$), 2.44 (t, 2H, CH2), 2.34 (t, 2H, CH$_2$), 1.88 (m, 2H, CH$_2$), 1.16 (d, 12H, CH(CH$_3$))

C. N,N'-bis(isopropyl)-5-[(4-carboxy-1-oxobutyl)-amino]-2,4,6-triiodo-1,3-benzenedicarboxyamide Using the methodology of Example 10, part B, the title product was prepared from the part B intermediate of this Example.

What is claimed is:

1. A radiolabeled protein of the formula:

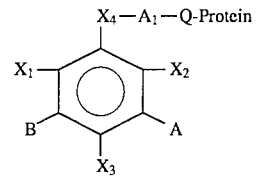

wherein $X_1$, $X_2$ and $X_3$ are independently selected from halogen and where at least one of $X_1$, $X_2$, $X_3$ is a radiohalogen;

$A_1$ is a single bond or a $C_{1-12}$ alkyl spacer group;

Q is a functional group suitable for conjunction to a protein and has or lacks a leaving group;

A and B are independently hydrogen, —CH$_2$—N—R$_2$, —C—N—R$_2$ or —C—R$_3$ where $R_1$ and $R_2$ are independently hydrogen, alkyl, hydroxyalkyl or acyloxyalkyl; and $R_3$ is —OH, —O-alkyl, —O-hydoxyalkyl, O-alkoxyalkyl, O-aminoalkyl, —NH-hydroxyalkyl or —NH-carboxy alkyl.

2. The radiolabeled protein of claim 1 wherein the protein is selected from monoclonal antibodies, antibody fragments, plasma proteins, polypeptides, hormones and carbohydrates.

3. The radiolabeled protein of claim 1 wherein said protein is a monoclonal antibody selected from chimeric L6, chimeric BR96, murine L6 and murine BR96.

4. The radiolabeled protein of claim 1 wherein further including a carrier interposed said functional group Q and said protein.

5. The radiolabeled protein of claim 4 wherein said carrier is an amino acid polymer.

6. The radiolabeled protein of claim 1 having the name murine L6 labeled with [I-125]-5-[(4-carboxy- 1-oxobutyl)amino]-2,4,6-triiodo-1,3-benzenedicarboxylic acid, dimethyl ester.

7. The radiolabeled protein of claim 1 having the name ChiL6 labeled with [I-125]-5-[(4-carboxy- 1-oxobutyl)-amino]-2,4,6-triiodo-1,3-benzenedicarboxylic acid, dimethyl ester.

8. The radiolabeled protein of claim 1 having the name ChiBR96 labeled with [I-125]-5-[(4-carboxy- 1-carboxy-1-oxoybutyl)methylamino]-2,4,6-triiodo-1,3-benzenedicarboxylic acid, dimethyl ester.

9. The radiolabeled protein of claim 1 having the name ChiL6 labeled with [I-125]-5-[(4-carboxy- 1-oxobutyl)methylamino]-2,4,6-triiodo-1,3-benzenedicarboxylic acid, dimethyl ester.

10. A method for radiolabeling a protein comprising coupling a radiolabeled compound of claim 1 with a protein.

* * * * *